(12) United States Patent
Shinohara et al.

(10) Patent No.: US 7,666,673 B2
(45) Date of Patent: Feb. 23, 2010

(54) METHOD OF GROWING SPERM STEM CELLS IN VITRO, SPERM STEM CELLS GROWN BY THE METHOD, AND MEDIUM ADDITIVE KIT TO BE USED IN GROWING SPERM STEM CELLS IN VITRO

(75) Inventors: Takashi Shinohara, Kyoto (JP); Mito Shinohara, Kyoto (JP)

(73) Assignee: Kyoto University, Kyoto-shi (JP)

( * ) Notice: Subject to any disclaimer, the term of this patent is extended or adjusted under 35 U.S.C. 154(b) by 462 days.

(21) Appl. No.: 10/553,118

(22) PCT Filed: Mar. 31, 2004

(86) PCT No.: PCT/JP2004/004612

§ 371 (c)(1),
(2), (4) Date: Nov. 3, 2005

(87) PCT Pub. No.: WO2004/092357

PCT Pub. Date: Oct. 28, 2004

(65) Prior Publication Data

US 2006/0265774 A1 Nov. 23, 2006

(30) Foreign Application Priority Data

Apr. 15, 2003 (JP) .............................. 2003-110821

(51) Int. Cl.
*C12N 5/00* (2006.01)
*C12N 5/02* (2006.01)
*C12N 5/08* (2006.01)

(52) U.S. Cl. ...................... 435/373; 435/325; 435/366; 435/383; 435/384; 435/392

(58) Field of Classification Search ................. 435/373, 435/325, 366, 383, 384, 392
See application file for complete search history.

(56) References Cited

U.S. PATENT DOCUMENTS

2007/0202590 A1 8/2007 Shinohara et al.

FOREIGN PATENT DOCUMENTS

EP 1 741 776 A1 1/2007

OTHER PUBLICATIONS

Creemers et al. Reproduction, 124: 791-799, 2002.*
Human embryology, Embryogenesis. http://www.embryology.ch/anglais/cgametogen/spermato03.html, accessed online on May 15, 2008.*
Wahab-Wahlgren Mol. And Cell. Endocrin., 201: 39-46, Mar. 28, 2003.*
Haneji et al. J. Endocrin., 128: 383-388, 1991.*
Ryu et al. PNAS, 102(40): 14302-14307, Oct. 2005.*
Brinster et al., *Proc. Natl. Acad. Sci. USA*, 91: 11298-11302 (1994).
Feng et al., *Science*, 297: 392-395 (2002).
Hasthorpe et al., *J. Reproduction and Fertility*, 119: 85-91 (2000).
Izadyar et al., *Biology of Reproduction*, 68: 272-281 (2003).
Kanatsu-Shinohara et al., *Biology of Reproduction*, 69: 612-616 (2003).
Meng et al., *Science*, 287: 1489-1493 (2000).
Miyasaka et al., *Life Science Shiko Zaidan Nenpo, Heisei 14 Nenban*, 17-19 (2003).
Nagano et al., *Tissue & Cell*, 30(4): 389-397 (1998).
Nagano et al., *FEBS Lett.*, 475: 7-10 (2000).
Nagano et al., *Proc. Natl. Acad. Sci. USA*, 98(23): 13090-13095 (2001).
Nagano et al., *Biology of Reproduction*, 68: 2207-2214 (2003).
Orwig et al., *Biology of Reproduction*, 67: 874-879 (2002).
Sariola, *Cell. Mol. Life Sci.*, 58(8): 1061-1066 (2001).
Shinohara et al., *Gendai Kagaku Zokan 41 Saisei Igaku Saisei Iryo*, 24-28 (2002).
Van Pelt et al., *Endocrinology*, 143(5): 1845-1850 (2002).
Lenhard et al., *Molecular and Cellular Neuroscience*, 20(2): 181-197 (2002).
Airaksinen et al., *Nature Reviews*, 3: 383-394 (2002).

* cited by examiner

*Primary Examiner*—Thaian N Ton
(74) *Attorney, Agent, or Firm*—Leydig, Voit & Mayer, Ltd.

(57) ABSTRACT

The present invention provides a method of growing spermatogonial stem cells of mammals and the like in vitro, which is characterized in that glial cell-derived neurotrophic factor (GDNF) or an equivalent thereto, and leukemia inhibitory factor (LIF) are contained in a medium (culture broth) for culturing spermatogonial stem cells. According to the method of the present invention, spermatogonial stem cells can be grown in vitro to the extent that enables use thereof for developmental engineering.

7 Claims, 6 Drawing Sheets

METHOD OF GROWING SPERM STEM CELLS IN VITRO, SPERM STEM CELLS GROWN BY THE METHOD, AND MEDIUM ADDITIVE KIT TO BE USED IN GROWING SPERM STEM CELLS IN VITRO

TECHNICAL FIELD

The present invention relates to a method of growing spermatogonial stem cells of mammals and the like in vitro, spermatogonial stem cells grown using the method, a medium additive kit to be used in growing spermatogonial stem cells in vitro, a method of producing a transgenic animal using the spermatogonial stem cells, and the like.

BACKGROUND ART

Spermatogonial stem cells of the mammalian testis are cells that keep growing limitlessly in the adult body to serve as a source of spermatogenesis via meiosis. Spermatogonial stem cells are dispensed to inherit genes to the next generation. Because spermatogonial stem cells are the only type of stem cells found in the adult body, they are useful for in vivo experiments, medical research, and biotechnology.

Brinster et al. succeeded in transplanting spermatogonial stem cells in vivo in 1994 (see "Brinster R L, Zimmermann J W, Spermatogenesis following male germ-cell transplantation, Proc Natl Acad Sci USA, 1994, Vol. 91, pp. 11298-11302"). In this method, when stem cells are transplanted into a seminiferous tubule, which constitutes the testis, they colonize and cause spermatogenesis of donor cell origin, whereby offspring can be produced. Thereby, the new possibility for manipulating germ line cells, in addition to ES cells, was pioneered, and a new field called developmental engineering using spermatogonial stem cells was established. Furthermore, a recent study reported that some spermatogonial stem cells are capable of surviving in vitro for 3 months or more (see "Nagano M, Avarbock M R, Leonida E B, Brinster C J, Brinster R L, Culture of mouse spermatogonial stem cells, Tissue Cell, 1998, Vol. 30, pp. 389-397"). In "Feng L-X, Chen Y, Dettin L, Reijo Pera R A, Herr J C, Goldberg E, Dym M, Generation and in vitro differentiation of a spermatogonial cell line, Science, 2002, Vol. 297, pp. 392-395", "van Pelt A M M, Roepers-Gajadien H L, Gademan I S, Creemers L B, de Rooij D G, van Dissel-Emiliani F M F, Establishment of cell lines with rat spermatogonial stem cell characteristics, Endocrinology, 2002, Vol. 143, pp. 1845-1850" and Japanese Patent Kohyo Publication No. 2001-517927 (publication date: Oct. 9, 2001), methods of growing or long maintaining spermatogonial stem cells are described.

Meantime, methods of preparing transgenic animals (particularly knockout animals) using various biotechnological techniques have recently been developed, and are utilized for preparation of knockout animals, breed improvement of domestic animals, and the like. As examples of such methods of preparing a transgenic animal, the somatic cell nuclear transfer method, the method using ES cells, the method of gene injection to pronucleus, and the like can be mentioned.

Although the somatic cell nuclear transfer method is considered to be the only currently available method enabling production of knockout animals in domestic animals such as bovines and swine, it is problematic in that the efficiency is very low, malformations are prevalent, and it is hence expensive.

The method using ES cells is now effectively utilized for mice, since it enables convenient, efficient preparation of knockout animals. However, in any animals other than mice (for example, domestic animals such as swine and bovines, and primates), no ES cells capable of producing germ cells have been collected to date, nor is there any report of knockout achieved by this technique. Additionally, preparing germ line cells using ES cells is also problematic in that the ES cells are likely to differentiate into cells other than germ line and thus lose the capacity of germ cell formation.

Additionally, the method of gene injection to pronucleus is a standard method for preparation of transgenic mice, and is already in practical use. For animals other than mice, however, the success rate is very low (for example, around 1% for swine and 1% or less for bovines) and the method is very expensive and unrealistic.

Provided that the above-described spermatogonial stem cells can be utilized in such preparation of transgenic animals, the same technique as with ES cells would be applicable because stem cells are capable of growing limitlessly, leading to the expectation that knockout animals can be prepared conveniently and efficiently.

However, there have been no successful attempts to grow these cells in vitro to the extent that permits practical application thereof, and to manipulate them.

Specifically, with the method described in "Nagano M, Avarbock M R, Leonida E B, Brinster C J, Brinster R L, Culture of mouse spermatogonial stem cells, Tissue Cell, 1998, Vol. 30, pp. 389-397", spermatogonial stem cells reportedly survived in vitro for 3 months or more, but no evidence for stem cell proliferation is given. Additionally, the methods of cultivation described in Japanese Patent Kohyo Publication No. 2001-517927, "Feng L-X, Chen Y, Dettin L, Reijo Pera R A, Herr J C, Goldberg E, Dym M, Generation and in vitro differentiation of a spermatogonial cell line, Science, 2002, Vol. 297, pp. 392-395", "van Pelt A M M, Roepers-Gajadien H L, Gademan I S, Creemers L B, de Rooij D G, van Dissel-Emiliani F M F, Establishment of cell lines with rat spermatogonial stem cell characteristics, Endocrinology, 2002, Vol. 143, pp. 1845-1850" and the like are problematic in that extraneous genes cannot be stably introduced to spermatogonial stem cells, and are also problematic in that no offspring derived from the spermatogonial stem cells cannot be obtained. Although spermatogonial stem cells can survive when cultured in vitro using one of the above-described methods of cultivation, the number of cells decreases to about 20% of the original number in 1 week under the present situation, and it is impossible to grow the cells. Hence, the conventional techniques are subject to limitation in manipulating spermatogonial stem cells to apply for biotechnology and the like. Additionally, no cases of actual spermatogenesis using spermatogonial stem cells cultured in vitro persistently for a long time have been reported to date.

DISCLOSURE OF THE INVENTION

The present invention has been developed in view of the above-described problems, and provides a method of growing spermatogonial stem cells that are effectively utilizable for in vivo experiments, medical research, and biotechnology, in vitro to the extent that permits utilization thereof for developmental engineering, spermatogonial stem cells grown using the method, and a medium additive kit to be used in growing spermatogonial stem cells in vitro.

The present inventors diligently investigated methods of growing spermatogonial stem cells in vitro, and found that when spermatogonial stem cells isolated from the testis of a neonatal mouse are cultured in the presence of glial cell-derived neurotrophic factor (GDNF) or an equivalent thereto and leukemia inhibitory factor (LIF), they can be grown ($10^{14}$ fold) over a period of 5 months or more. Furthermore, the present inventors transplanted cultured spermatogonial stem cells to the seminiferous tubule, found that the fertility of a congenitally infertile mouse can be restored, and developed the present invention.

Accordingly, the present application relates to the following:

(1) A method of growing spermatogonial stem cells, which comprises growing spermatogonial stem cells by culturing the spermatogonial stem cells using a medium containing glial cell-derived neurotrophic factor (GDNF) or an equivalent thereto and leukemia inhibitory factor (LIF).

(2) The method of growing spermatogonial stem cells described in (1) above, wherein the above-described medium further contains at least one of epidermal growth factor (EGF) and basic fibroblast growth factor (bFGF).

(3) The method of growing spermatogonial stem cells described in (1) or (2) above, wherein the above-described medium further contains serum.

(4) The method of growing spermatogonial stem cells described in any one of (1) to (3) above, which further comprises using feeder cells.

(5) The method of growing spermatogonial stem cells described in any one of (1) to (4) above, which comprises using mammal-derived spermatogonial stem cells.

(6) The method of growing spermatogonial stem cells described in any one of (1) to (5) above, wherein the above-described glial cell-derived neurotrophic factor (GDNF) or an equivalent thereto is contained at a concentration of 0.5 to 50 ng/ml in the above-described medium.

(7) The method of growing spermatogonial stem cells described in any one of (1) to (6) above, wherein the above-described leukemia inhibitory factor (LIF) is contained at a concentration of $10^2$ to $10^4$ units/ml in the above-described medium.

(8) The method of growing spermatogonial stem cells described in any one of (2) to (7) above, wherein epidermal growth factor (EGF) is contained at a concentration of 0.5 to 50 ng/ml in the above-described medium.

(9) The method of growing spermatogonial stem cells described in any one of (2) to (8) above, wherein the above-described basic fibroblast growth factor (bFGF) is contained at a concentration of 0.5 to 50 ng/ml in the above-described medium.

(10) The method of growing spermatogonial stem cells described in any one of (3) to (9) above, wherein the above-described serum is contained at a concentration of 0.1 to 5(v/v) % in the medium at the start of cultivation of the above-described spermatogonial stem cells, and at a concentration of 0.1 to 20(v/v) % in the medium after passage of the above-described spermatogonial stem cells.

(11) The method of growing spermatogonial stem cells described in any one of (4) to (10) above, wherein the above-described feeder cells are used by 4 weeks after the start of cultivation at latest.

(12) Spermatogonial stem cells grown in vitro using the growing method described in any one of (1) to (11) above.

(13) A therapeutic agent for infertility containing the spermatogonial stem cells described in (12) above.

(14) A medium additive kit that comprises glial cell-derived neurotrophic factor (GDNF) or an equivalent thereto and at least one of epidermal growth factor (EGF) and basic fibroblast growth factor (bFGF), and that is used as added to a culture medium for growing spermatogonial stem cells in vitro.

(15) The medium additive kit described in (12) above, which further comprises leukemia inhibitory factor (LIF).

(16) The medium additive kit described in (14) or (15) above, which further comprises serum.

(17) Use of the spermatogonial stem cells described in (12) above for producing a therapeutic agent for infertility.

(18) A therapeutic method for infertility using the spermatogonial stem cells described in (12) above.

(19) A method of producing a non-human animal that forms sperms derived from transplanted spermatogonial stem cells, which comprises the following steps:
a) a step of growing spermatogonial stem cells by culturing the spermatogonial stem cells using a medium containing glial cell-derived neurotrophic factor (GDNF) or an equivalent thereto and leukemia inhibitory factor (LIF);
b) a step of transplanting the spermatogonial stem cells grown in step a) into a seminiferous tubule of an infertile non-human animal to obtain a non-human animal showing spermatogenesis derived from the spermatogonial stem cells.

(20) A method of producing sperm, which comprises the following steps:
a) a step of growing spermatogonial stem cells by culturing the spermatogonial stem cells using a medium containing glial cell-derived neurotrophic factor (GDNF) or an equivalent thereto and leukemia inhibitory factor (LIF);
b) a step of transplanting the spermatogonial stem cells grown in step a) into a seminiferous tubule of an infertile non-human animal to obtain a non-human animal showing spermatogenesis derived from the spermatogonial stem cells;
c) a step of obtaining sperm from the non-human animal.

(21) A method of producing an embryo derived from spermatogonial stem cells, which comprises the following steps:
a) a step of growing spermatogonial stem cells by culturing the spermatogonial stem cells using a medium containing glial cell-derived neurotrophic factor (GDNF) or an equivalent thereto and leukemia inhibitory factor (LIF);
b) a step of transplanting the spermatogonial stem cells grown in step a) into a seminiferous tubule of an infertile non-human animal to obtain a non-human animal showing spermatogenesis derived from the spermatogonial stem cell;
c) a step of obtaining sperm from the non-human animal;
d) a step of inseminating an ovum with the sperm to obtain an embryo.

(22) A method of producing non-human offspring derived from spermatogonial stem cells, which comprises the following steps:
a) a step of growing spermatogonial stem cells by culturing the spermatogonial stem cells using a medium containing glial cell-derived neurotrophic factor (GDNF) or an equivalent thereto and leukemia inhibitory factor (LIF);
b) a step of transplanting the spermatogonial stem cells grown in step a) into a seminiferous tubule of an infertile non-human animal to obtain a non-human animal showing spermatogenesis derived from the spermatogonial stem cells;
c) a step of obtaining sperm from the non-human animal;
d) a step of inseminating an ovum with the sperm to obtain an embryo;
e) a step of transferring the embryo into an oviduct of a pseudopregnant female to obtain non-human offspring.

(23) A method of producing non-human offspring derived from spermatogonial stem cells, which comprises the following steps:
a) a step of growing spermatogonial stem cells by culturing the spermatogonial stem cells using a medium containing glial cell-derived neurotrophic factor (GDNF) or an equivalent thereto and leukemia inhibitory factor (LIF);
b) a step of transplanting the spermatogonial stem cells grown in step a) into a seminiferous tubule of an infertile non-human animal to obtain a non-human animal showing spermatogenesis derived from the spermatogonial stem cells;

c) a step of naturally mating the non-human animal with a female to obtain non-human offspring.

(24) A method of producing spermatogonial stem cells incorporating an extraneous gene, which comprises the following steps:

a) a step of growing spermatogonial stem cells by culturing the spermatogonial stem cells using a medium containing glial cell-derived neurotrophic factor (GDNF) or an equivalent thereto and leukemia inhibitory factor (LIF);

b) a step of introducing an extraneous gene to the spermatogonial stem cells grown in step a) to obtain spermatogonial stem cells incorporating the extraneous gene.

(25) A method of producing sperm incorporating an extraneous gene, which comprises the following steps:

a) a step of growing spermatogonial stem cells by culturing the spermatogonial stem cells using a medium containing glial cell-derived neurotrophic factor (GDNF) or an equivalent thereto and leukemia inhibitory factor (LIF);

b) a step of introducing an extraneous gene to the spermatogonial stem cells grown in step a) to obtain spermatogonial stem cells incorporating the extraneous gene;

c) a step of inducing spermatogenesis by transplanting the spermatogonial stem cells to a seminiferous tubule to obtain sperm incorporating the exogenous gene.

(26) A method of producing a transgenic non-human animal, which comprises the following steps:

a) a step of growing spermatogonial stem cells by culturing the spermatogonial stem cells using a medium containing glial cell-derived neurotrophic factor (GDNF) or an equivalent thereto and leukemia inhibitory factor (LIF);

b) a step of introducing an extraneous gene to the spermatogonial stem cells grown in step a) to obtain spermatogonial stem cells incorporating the extraneous gene;

c) a step of inducing spermatogenesis by transplanting the spermatogonial stem cells to a seminiferous tubule to obtain sperm incorporating the exogenous gene;

d) a step of inseminating an ovum with the sperm to obtain a transgenic non-human animal.

(27) The production method described in (26) above, wherein the transgenic non-human animal is a knockout non-human animal.

As described above, the method of the present invention of growing spermatogonial stem cells comprises growing spermatogonial stem cells by culturing the spermatogonial stem cells using a medium containing glial cell-derived neurotrophic factor (GDNF) and leukemia inhibitory factor (LIF).

According to the above-described method, it becomes possible to grow spermatogonial stem cells, which have not permitted long-term growth in vitro. Thereby, it becomes possible to effectively utilize spermatogonial stem cells, which have been subject to limitation as to range of application due to the lack of an efficient growing method despite the expectation for application to various fields.

Also, because the spermatogonial stem cells of the present invention obtained by the above-described method have been grown to the extent that permits practical application thereof, they can be utilized for developmental engineering in various fields, including in vivo experiments, medical research, biotechnology and the like.

BRIEF DESCRIPTION OF THE DRAWINGS

FIG. 1(a) to (e) show the results of a microscopic observation of the development of testis cells of a neonatal mouse to GS cell colonies, in Example 1. (a) shows floating cells collected from a gelatin-coated plate after 1 DIV. (b) shows the beginning of the formation of small colonies by cells at 4 DIV. (c) shows a GS cell colony at 8 DIV. (d) shows a GS colony on MEF feeder cells at 95 DIV. (e) shows chain formation by proliferating cells at 95 DIV.

FIG. 3(a) to (f) are graphs showing the results of characterization of cultured cells by flow cytometry using respective molecular markers in Example 1. Note that the graphs in (a) to (f) show the results obtained using $\alpha$6-integrin, $\beta$1-integrin, EpCAM, EE2, c-kit, and SSEA-1 as molecular markers, arranged in the order from (a), respectively.

BEST MODE OF EMBODIMENT OF THE INVENTION

The method of the present invention of growing spermatogonial stem cells comprises growing spermatogonial stem cells by culturing the spermatogonial stem cells using a medium containing glial cell-derived neurotrophic factor (GDNF) or an equivalent thereto and leukemia inhibitory factor (LIF).

Accordingly, it can be said that a feature of the above-described method of growing spermatogonial stem cells resides in that glial cell-derived neurotrophic factor (GDNF) or an equivalent thereto and leukemia inhibitory factor (LIF) are contained in a medium (culture broth) for culturing spermatogonial stem cells. Therefore, when culturing spermatogonial stem cells to embody the growing method of the present invention, culture conditions other than the feature can be selected according to a conventionally known method.

The term "equivalent to glial cell-derived neurotrophic factor (GDNF) " as used herein encompasses GDNF-like compounds such as neurturin, persephin, and artemin, and other compounds exhibiting an action similar to that of glial cell-derived neurotrophic factor (GDNF) or a GDNF-like compound on a GDNF receptor(s) or an co-receptor(s) (for example, antibodies that specifically recognize a GDNF receptor(s) or an co-receptor(s), agonistic compounds to a GDNF receptor(s) or an co-receptor(s), and the like). As such, the receptor(s) or co-receptor(s) include Ret tyrosine kinase and the GDNF-family receptor α:s, respectively.

A GDNF-like compound means a compound that is structurally similar to glial cell-derived neurotrophic factor (GDNF), or that acts like glial cell-derived neurotrophic factor (GDNF) on a receptor or co-receptor thereof. As the GDNF-like compound, neurturin, persephin, artemin and the like, in particular, can be mentioned.

Glial cell-derived neurotrophic factor (GDNF) and GDNF-like compounds are structurally similar to each other; cRet receptor tyrosine kinase acts as a common signal transmission receptor shared by glial cell-derived neurotrophic factor (GDNF), neurturin, persephin, and artemin.

"A compound that acts like glial cell-derived neurotrophic factor (GDNF)" means a compound that acts in the same manner as glial cell-derived neurotrophic factor (GDNF) on a receptor that transmits the signal of glial cell-derived neurotrophic factor (GDNF) or a co-receptor thereof.

"A GDNF receptor" means a substance that binds to glial cell-derived neurotrophic factor (GDNF) or a GDNF-like compound, i.e., a compound capable of transmitting the signal of glial cell-derived neurotrophic factor (GDNF) or a GDNF-like compound. As the "GDNF receptor", cRet receptor tyrosine kinase, which is a receptor that mediates a signal for glial cell-derived neurotrophic factor (GDNF) or GDNF-like compound, in particular, can be mentioned.

"A GDNF co-receptor" means a receptor that does not transmit the signal of GDNF or a GDNF-like compound but activates a receptor that transmits the signal of GDNF or a GDNF-like compound. These compounds, in particular, are receptors whose members are called the GDNF family receptor α:s (GFRα). These are also associated with signaling receptor complexes for GDNF, persephin, artemin, and neurturin. As receptors of the family, 4 members (GFRα 1 to 4) (Jing, S., et al., Cell, 85, 9-10 (1996); Jing, S. Q., et al., J. Biol. Chem., 272, 33111-33117 (1997); Trean or, J. J., et al., Nature, 382, 80-83 (1996); Subanto, P., et al., Human Molecular Genetics, 6, 1267-1273 (1997)) are already known. These are capable of independently transmitting signals, all of which are essential to ligand binding and cRet activation.

According to the above-described method, it becomes possible to culture spermatogonial stem cells, which have not permitted long-term cultivation in vitro. Thereby, it becomes possible to effectively utilize spermatogonial stem cells, which have been subject to limitation as to range of application due to the lack of an efficient growing method despite the expectation for application to various fields.

Specifically, spermatogonial stem cells are applicable to preparation of transgenic animals, treatment and drugs for human male infertility, research and drug development for gene therapy at the human germ cell level, and the like. Also, because these applications essentially require a sep of growing spermatogonial stem cells, the method of the present invention of growing spermatogonial stem cells is very effective and can be said to be highly valuable.

In the method of the present invention of growing spermatogonial stem cells, it is preferable that at least one of epidermal growth factor (EGF) and basic fibroblast growth factor (bFGF) be further contained in the above-described medium.

Generally, stable cell culture can be performed, provided that one of EGF and bFGF is contained in the cultivation of stem cells. Hence, in the case of the present invention as well, stable spermatogonial stem cell culture can be performed, provided that at least one of EGF and bFGF is contained.

In the method of the present invention of growing spermatogonial stem cells, the above-described medium can further contain a serum. As the serum, and serum known per se can be used, and examples of preferably used sera include, but are not limited to, for example, fetal calf serum (FCS) and the like.

Additionally, in the method of the present invention of growing spermatogonial stem cells, spermatogonial stem cells may be cultured using feeder cells. Examples of preferably used feeder cells include, but are not limited to, mouse embryonic fibroblasts (MEF) and the like.

In the method of the present invention of growing spermatogonial stem cells, spermatogonial stem cells derived from a mammal are preferably used.

As examples of the above-described mammal, laboratory animals such as mice, rats, and rabbits, domestic animals such as swine, bovines, and goat, and primates such as humans, monkeys, orangutans, and chimpanzees can be mentioned. The above-described laboratory animals are literally useful as experimental animals for the development of pharmaceuticals and the like. The above-described domestic animals are also used for food and the like, and are useful for human life. Also, primates are useful, because they are taxonomically closer to humans and can be utilized for elucidating the mechanisms of various diseases in humans, for elucidating the mechanisms of germ cell differentiation, and the like.

Hence, according to the above-described method, it is possible to grow spermatogonial stem cells of mammals that are useful in various fields, including in vivo experiments, medical research, biotechnology, animal farming, and the like, and the method can be said to be of high value.

In the method of the present invention of growing spermatogonial stem cells, the above-described glial cell-derived neurotrophic factor (GDNF) or an equivalent thereto is usually contained in the above described medium at a concentration of 0.05 ng/ml to 100 mg/ml, for example, 0.5 ng/ml to 100 μg/ml, preferably 0.5 ng/ml to 10 μg/ml, more preferably 0.5 ng/ml to 1 μg/ml, still more preferably 0.5 to 200 ng/ml, and still yet more preferably 0.5 to 50 ng/ml.

Additionally, in the method of the present invention of growing spermatogonial stem cells, the above-described leukemia inhibitory factor (LIF) is usually contained in the above-described medium at a concentration of 10 to $10^6$ units/ml, for example, 10 to $10^5$ units/ml, preferably at $10^2$ to $10^4$ units/ml.

Furthermore, in the method of the present invention of growing spermatogonial stem cells, provided that epidermal growth factor (EGF) is contained in the above-described medium, the concentration thereof is usually 0.05 ng/ml to 100 mg/ml, for example, 0.5 ng/ml to 100 μg/ml, preferably 0.5 ng/ml to 10 μg/ml, more preferably 0.5 ng/ml to 1 μg/ml, still more preferably 0.5 to 200 ng/ml, and still yet more preferably 0.5 to 50 ng/ml.

Additionally, in the method of the present invention of growing spermatogonial stem cells, provided that the above-described basic fibroblast growth factor (bFGF) is contained in the above-described medium, the concentration thereof is usually 0.05 ng/ml to 100 mg/ml, for example, 0.5 ng/ml to 100 μg/ml, preferably 0.5 ng/ml to 10 μg/ml, more preferably 0.5 ng/ml to 1 μg/ml, still more preferably 0.5 to 200 ng/ml, and still yet more preferably 0.5 to 50 ng/ml.

Additionally, in the method of the present invention of growing spermatogonial stem cells, provided that the above-described serum is contained in the above-described medium, it is preferable that the serum be contained at a concentration of 0.1 to 5(v/v) % in the medium at the start of cultivation of the above-described spermatogonial stem cells, and at a concentration of 0.1 to 20(v/v) % in the medium after passage of the above-described spermatogonial stem cells.

Provided that the above-described medium for culturing spermatogonial stem cells contains the individual factors (GDNF or an equivalent thereto, EGF, bFGF, LIF, and serum) at the concentrations as described above, it is possible to further stabilize the cultivation of spermatogonial stem cells, and to increase the proliferation rate of spermatogonial stem cells.

Furthermore, in the method of the present invention of growing spermatogonial stem cells, the above-described feeder cells are preferably used by 4 weeks after the start of cultivation at latest.

According to the above-described method, spermatogonial stem cells adhere to feeder cells, and can colonize efficiently.

The spermatogonial stem cells of the present invention are the cells which have been grown in vitro by the above-described growing method.

Because the above-described spermatogonial stem cells have been grown to the extent that permits practical application thereof by the above-described growing method, they can be utilized for developmental engineering in various fields, including in vivo experiments, medical research, biotechnology and the like.

Note that as an example of a method of utilizing the above-described spermatogonial stem cells, a method utilizing them as a drug for the treatment of human male infertility can be mentioned. Hence, therapeutic agents for infertility containing the above-described spermatogonial stem cells are also included in the scope of the present invention.

Additionally, the medium additive kit of the present invention comprises glial cell-derived neurotrophic factor (GDNF) or an equivalent thereto and at least one of epidermal growth factor (EGF) and basic fibroblast growth factor (bFGF), and is used as added to a culture medium for growing spermatogonial stem cells in vitro.

According to the above-described composition, it is possible to cultivate spermatogonial stem cells to high extents, which have conventionally been difficult to grow, by adding to a medium for culturing spermatogonial stem cells in vitro. Note that at the start of cultivation of spermatogonial stem cells, LIF is also an essential factor, in addition to the above-described factors, i.e., GDNF or an equivalent thereto and EGF and/or bFGF. Because the above-described medium additive kit does not contain LIF, it is preferable that the kit be utilized as a medium additive kit in maintaining a culture after the spermatogonial stem cell culture in established (i.e., as an additive kit for a culture medium after passage).

Additionally, when using the above-described medium additive kit at the start of cultivation of spermatogonial stem cells, it is also possible to add and utilize LIF, separately from the above-described medium additive kit, and the above-described medium additive kit may further contain leukemia inhibitory factor (LIF).

Additionally, the above-described medium additive kit may further contain the above-described serum.

According to the above-described composition, the kit can be suitably utilized as a medium additive kit that simplifies medium preparation at the start of cultivation of spermatogonial stem cells, and in addition, provided that the above-described medium additive is added to the medium during maintenance of a culture of spermatogonial stem cells, the growth efficiency of spermatogonial stem cell can be further increased.

The present invention is hereinafter described in more detail, but is never limited to the description.

In this mode of embodiment, a method of growing mammalian spermatogonial stem cells in vitro, in particular, is described. This method of growing mammalian spermatogonial stem cells comprises growing the cells using a culture medium containing glial cell-derived neurotrophic factor (GDNF) or an equivalent thereto, epidermal growth factor (EGF), basic fibroblast growth factor (bFGF), leukemia inhibitory factor (LIF), and fetal calf serum (FCS) as a serum, with mouse embryonic fibroblasts (MEF) as feeder cells.

Referring to a more specific case of mouse spermatogonial stem cells, the method of growing spermatogonial stem cells in this mode of embodiment can be performed per the procedures shown in (1) to (5) below.

(1) The testis of a just born mouse is totally digested with collagenase, trypsin, and DNase.
(2) The testis cells thus rendered single cells (dispersed) are allocated onto a gelatin-coated plate. The culture broth (i.e., medium) used here is based on, for example, Stem-Pro-34, and contains a plurality of cell growth factors, i.e., glial cell-derived neurotrophic factor (GDNF) or an equivalent thereto, epidermal growth factor (EGF), basic fibroblast growth factor (bFGF), and leukemia inhibitory factor (LIF), and fetal calf serum (FCS).
(3) In 10 days to 2 weeks after the start of cultivation, trypsin treatment is performed and the cells are passaged at a 1-fold or ½-fold concentration.
(4) After the passage described in (3) is repeated two or three times, the cultured cells are transferred onto mouse embryonic fibroblasts (MEF), which are feeder cells, and cultivation is continued. As stated here, it is preferable that spermatogonial stem cells be transferred onto mouse embryonic fibroblasts (MEF) by the time after passage is repeated two or three times, i.e., by 4 weeks after the start of cultivation at latest.
(5) In 3 to 4 weeks after the start of cultivation, germ cell colonies stabilize; thereafter, passage is continued with trypsin treatment at a ⅓ to ¼ dilution rate at intervals of 3 to 5 days for several months.

When growing mouse spermatogonial stem cells in vitro per the above-described procedures, the cells can be grown up to $10^{14}$ fold in 5 months, compared to the beginning of cultivation, as described in Examples below.

Note that the number of spermatogonial stem cells in the mouse testis is very small and is estimated to be as few as about 2 to 3 cells per 10,000 testis cells. Even when these spermatogonial stem cells are cultured in vitro according to a conventional method, the number of cells decreases to about 20% of the starting number in about 1 week; no conditions that cause stem cell proliferation have been found. For this reason, it has been difficult to utilize spermatogonial stem cells for developmental engineering despite the supposed wide applicability for developmental engineering.

In contrast, according to the method of the present invention of growing spermatogonial stem cells, it has become possible to grow the cells for a long period to high extents. Furthermore, spermatogonial stem cells obtained by this growing method have been confirmed to cause spermatogenesis derived from the spermatogonial stem cells for a long period, and to be capable of producing offspring derived from the sperm thereof when transplanted into a seminiferous tubule of an infertile mouse, as shown in Examples. Specifically, the sperm derived from spermatogonial stem cells obtained by the method of the present invention of growing spermatogonial stem cells have been confirmed to function as actual sperm.

Hence, spermatogonial stem cells obtained by this growing method are expected to be effectively utilized for various technical developments in the various fields including in vivo experiments, medical research, and biotechnology. Note that this method of growing spermatogonial stem cells is the first technique that was confirmed to allow persistent growth of spermatogonial stem cells and clearly shown to enable the formation of sperm derived therefrom and the production of offspring derived from the sperm.

In this mode of embodiment, GDNF or an equivalent thereto, EGF, bFGF, LIF, and FCS are contained in the culture medium for spermatogonial stem cells, as described above. However, the present invention is not limited thereto, as long as at least glial cell-derived neurotrophic factor (GDNF) or an equivalent thereto and leukemia inhibitory factor (LIF) are contained in the above-described culture medium. As other constituents, those that have conventionally been used for the cultivation of spermatogonial stem cells and the like (for example, epidermal growth factor (EGF), basic fibroblast growth factor (bFGF), serum and the like) can be used as appropriate. Specific examples of the above-described medium are shown in Examples below.

Note that in the above-described method of culturing spermatogonial stem cells, GDNF or an equivalent thereto and LIF are essential ingredients for the medium used in establishing a culture (i.e., at the start of cultivation), but it is possible to maintain cells even if the above-described LIF is not contained in the medium used in maintaining culture after the culture is established (i.e., medium after passage). However, provided that the medium after passage contains the above-described LIF, the proliferation rate of the spermatogonial stem cell can be further increased.

Additionally, to increase the proliferation rate of the spermatogonial stem cell, the concentrations of the above-described growth factors and leukemia inhibitory factor in the medium are preferably 0.5 to 50 ng/ml for the above-described glial cell-derived neurotrophic factor (GDNF) or an equivalent thereto, preferably 0.5 to 50 ng/ml for epidermal growth factor (EGF), preferably 0.5 to 50 ng/ml for the above-described basic fibroblast growth factor (bFGF), and preferably $10^2$ to $10^4$ units/ml for the above-described leukemia inhibitory factor (LIF).

Additionally, regarding the above-described serum, provided that it is contained in the medium at the start of cultivation (i.e., first supply of medium in cultivation in vitro) at a low concentration of 0.1 to 5(v/v) %, it is possible to stably establish a culture of spermatogonial stem cells. Note that for any other medium (i.e., medium after passage), the serum may be contained at a higher concentration of up to 20(v/v) %.

Additionally, in another aspect, in the method of the present invention of growing spermatogonial stem cells, provided that the above-described serum is contained in the medium, the serum may be contained in the medium after passage of the above-described spermatogonial stem cells at a concentration of 10 to 20(v/v) %, preferably 15 to 20(v/v) %. In this case, even if the medium does not contain one or both of the above-described epidermal growth factor (EGF) and basic fibroblast growth factor (bFGF), it is possible to accomplish a very stable culture of spermatogonial stem cells.

Also, the concentration of the above-described growth factors and leukemia inhibitory factor in the medium are more preferably 2 to 20 ng/ml for the above-described glial cell-derived neurotrophic factor (GDNF) or an equivalent thereto, more preferably 2 to 30 ng/ml for epidermal growth factor (EGF), more preferably 2 to 20 ng/ml for the above-described basic fibroblast growth factor (bFGF), and more preferably $3 \times 10^2$ to $5 \times 10^3$ units/ml for the above-described leukemia inhibitory factor (LIF). Additionally, in the medium at the start of cultivation of spermatogonial stem cells, the concentration of the above-described serum is preferably 0.5 to 2(v/v) %. Provided that the factors are contained in the medium at the above-described concentrations, it is possible to securely establish a culture of spermatogonial stem cells, and to further increase the proliferation rate of the spermatogonial stem cell.

Hereunder, a method of utilizing the spermatogonial stem cells of the present invention, i.e., spermatogonial stem cells grown by the above-described method of cultivation, is described.

Because the spermatogonial stem cells of the present invention have been grown to high extents by the above-described growing method, they can be utilized for developmental engineering in various fields, including in vivo experiments, medical research, biotechnology and the like. As major applications for these spermatogonial stem cells, the following can be mentioned.

(a) Preparation of a novel transgenic animal
(b) Treatment for human male infertility
(c) Gene therapy at the human germ cell level In (a) above, spermatogenesis is performed by carrying out operations such as introduction of an extraneous gene to spermatogonial stem cells, which serve as the source of spermatogenesis, and transplanting the spermatogonial stem cells incorporating the extraneous gene to a seminiferous tubule. Subsequently, a transgenic animal can be prepared using a technique comprising inseminating an ovum with the thus-obtained sperm.

More specifically, as examples of the method of introducing an extraneous gene to spermatogonial stem cells, a method comprising introducing a vector constructed to allow the functional expression of a particular gene to spermatogonial stem cells can be mentioned. As the vector, a plasmid vector, a viral vector and the like can be used. Additionally, as the viral vector, retrovirus, adenovirus, lentivirus, herpesvirus, adeno-associated virus, parvovirus, Semliki forest fever virus, vaccinia virus and the like can be mentioned.

As examples of the method of introducing a vector to spermatogonial stem cells, common gene transfection methods such as the calcium phosphate method, the DEAE dextran method, the electroporation method, or the lipofection method can be mentioned. When using a virus as the vector, the virus' genome may be introduced to cells by one of the above-described common gene transfection methods, and the virus' genome can also be introduced to cells by infecting the cells with virus particles.

Additionally, by using the method of the present invention of growing spermatogonial stem cells, spermatogonial stem cells stably incorporating an extraneous gene can be selected. For example, a marker gene, simultaneously with a vector, may be introduced to spermatogonial stem cells, and the spermatogonial stem cells may be cultured by a method suitable for the properties of the marker gene. For example, when the marker gene is a gene that confers drug resistance to a selection drug that is lethal to the host spermatogonial stem cells, the spermatogonial stem cells incorporating a vector may be cultured using a medium supplemented with the drug. As examples of the combination of a drug-resistance-conferring gene and a selection drug, a combination of the neomycin-resistance-conferring gene and neomycin (G418), a combination of the hygromycin-resistance-conferring gene and hygromycin, a combination of the blasticidin-S-resistance-conferring gene and blasticidin S, and the like can be mentioned.

Additionally, it is also possible to obtain spermatogonial stem cells lacking a particular gene using the similar method. As an example of the method of obtaining spermatogonial stem cells lacking a particular gene, homologous recombination using a targeting vector (gene targeting method) can be mentioned. Specifically, spermatogonial stem cells lacking a particular gene can be obtained by isolating the chromosome DNA of the particular gene;

introducing, to the chromosome of spermatogonial stem cells by the homologous recombination method, a DNA strand (targeting vector) having a DNA sequence constructed to destroy the gene by inserting, to an exon portion of the gene, a drug resistance gene represented by the neomycin resistance gene or the hygromycin resistance gene, a reporter gene represented by lacZ (β-galactosidase gene), cat (chloramphenicol acetyltransferase gene) and the like to destroy the exon function, by inserting a DNA sequence that terminates gene transcription to the intron portion between exons (for example, polyA addition signal and the like) to prevent the synthesis of complete messenger RNA, and the like;

analyzing the thus-obtained cells by Southern hybridization analysis using a DNA sequence in the DNA of a particular gene or a DNA sequence in the vicinity of the DNA as a probe or by a PCR method with primers of the DNA sequence in the targeting vector and a DNA sequence in the vicinity of, but other than, the DNA of the particular gene used to prepare the targeting vector; and selecting spermatogonial stem cells lacking the particular gene. Alternatively, the Cre-loxP system, which deletes a particular gene in a tissue-specific or developmental-stage-specific manner, and the like may also be used (Marth, J. D. (1996) Clin. Invest. 97:1999-2002; Wagner, K. U. et al. (1997), Nucleic Acids Res. 25:4323-4330).

A transgenic animal can be prepared using the method comprising performing spermatogenesis by transplanting the thus-obtained spermatogonial stem cells incorporating an extraneous gene or spermatogonial stem cells lacking a particular gene to a seminiferous tubule of an infertile animal and the like, and inseminating an ovum with the thus-obtained sperm.

Although this method is similar to the method of preparing a transgenic animal utilizing ES cells, ES cells have multipotency to differentiate into cells other than germ line cells, and there are a risk of carcinogenesis when ES cells are transplanted to the seminiferous tubule. In contrast, when using the spermatogonial stem cells of the present invention, they are capable of forming normal sperms, without carcinogenesis, even when transplanted to the seminiferous tubule. Hence, when using the above-described spermatogonial stem cells, a transgenic animal can be prepared conveniently and efficiently. This preparation of a transgenic animal using spermatogonial stem cells has the potential for use as a method of preparing a transgenic animal in mammals such as domestic animals and primates for which no effective method of preparation of transgenic animal is available.

In (b) above, for example, spermatogonial stem cells are collected from the testis of a infertile patient by biopsy, and cultured in vitro by the growing method of the present invention. Subsequently, treatment can be performed by a method comprising injecting (microinjecting) proliferated spermatogonial stem cells into the infertile patient's seminiferous tubule to cause spermatogenesis derived from the cultured cells in the seminiferous tubule of the patient's testis. This method is particularly effective in cases where the patient has become infertile due, for example, to chemotherapy or radiotherapy.

As stated above, the above-described spermatogonial stem cells can be utilized for the treatment of human male infertility; therefore, therapeutic agents for infertility containing the above-described spermatogonial stem cells, especially those for males, also fall within the scope of the present invention.

The gene therapy at the human germ cell level described in (c) above is, for example, a therapeutic method for use in cases where a particular gene has a mutation, which comprises preparing spermatogonial stem cells in which the gene is replaced by a normally functioning gene so that the mutation will not be inherited to the offspring thereof. Even in such a therapeutic method, it is necessary to maintain and grow spermatogonial stem cells, and in this case, the method of the present invention of growing spermatogonial stem cells can be effectively utilized.

Next, the medium additive kit of the present invention is described. The medium additive kit of the present invention comprises glial cell-derived neurotrophic factor (GDNF) or an equivalent thereto and at least one of epidermal growth factor (EGF) and basic fibroblast growth factor (bFGF), and is used as added to a culture medium for growing spermatogonial stem cells in vitro. Also, this medium additive kit preferably further contains leukemia inhibitory factor (LIF). Additionally, the above-described medium additive kit can further contain the above-described serum.

The above-described medium additive kit can be used as added to a commonly used cell culture medium when culturing spermatogonial stem cells. By adding this medium additive kit, spermatogonial stem cells can be grown in vitro to high extents. More specifically, in the case of Examples, the cells can be grown $10^{14}$ fold in 5 months. Additionally, because the kit thus contains the various growth factors, leukemia inhibitory factor and serum in an appropriate mixing ratio, it enables convenient cultivation of spermatogonial stem cells.

Provided that leukemia inhibitory factor (LIF) is further contained in the above-described medium additive kit, the kit could be effectively utilized especially as an additive kit for a culture medium at the start of cultivation of spermatogonial stem cells. In addition, it is possible not only to further increase the proliferation rate of spermatogonial stem cells, but also to further simplify the preparation of medium as the need for separate addition of LIF is obviated.

Note that the mixing ratio of the individual growth factors, leukemia inhibitory factor and serum contained in the above-described medium additive kit is preferably composed such that the concentrations of the individual factors in the medium would fall within the above-described suitable ranges when they are added to the spermatogonial stem cell culture medium. Additionally, the above-described medium additive kit may contain as appropriate, in addition to the above-described substances, insulin, transferrin, BSA, 2-ME, estradiol, progesterone and the like, for the purpose of stably maintaining the above-described substances.

The Examples of the present invention are hereinafter described with reference to drawings, but the present invention is not limited by this description.

EXAMPLE 1

[1] Experimental Methods and Materials (1) Animals Used in the Experiment

First, the animals used in this experiment are described.

Testis cells were collected by two-step enzymatic digestion from a newborn transgenic mouse line C57BL6/Tg14 (act-EGFP-OsbY01) that was bred into DBA/2 mouse strain (provided by Dr. Okada, Osaka University), and used for culture (reference 1, Okabe M et. al., 'Green mice' as a source of ubiquitous green cells, FEBS Lett, vol. 407, pp. 313-319, 1997). The spermatogonia and spermatocytes of these mice express the EGFP gene, the level of expression decreases gradually after meiosis. Therefore, donor cells can be readily identified following transplantation.

Cultured cells were transplanted into BALB/c nude mouse or W pups mouse (5-10 days old, Japan SLC). To avoid endogenous spermatogenesis, nude mice were treated with busulfan (44 mg/kg) at 6 wk of age and were subsequently injected with corresponding bone marrow cells to reduce mortality. In experiments using W recipients, 50 μg of anti-CD4 antibody (GK1.5) was administrated intraperitoneally on Days 0, 2, and 4 after the transplantation to induce tolerance to the allogenic donor cells. All animal experimentation protocols were approved by the Institutional Animal Care and Use Committee of Kyoto University.

(2) Culture Conditions

Hereunder, the culture conditions for spermatogonial stem cells in this experiment are described.

Dissociated testis cells were allocated to gelatin-coated cell culture plate. Culture medium for the testis cells was StemPro-34 SFM (Invitrogen) supplemented with StemPro supplement (Invitrogen), 25 μg/ml Insulin, 100 μg/ml transferrin, 60 μM putrescine, 30 nM sodium selenite, 6 mg/ml D-(+)-glucose, 30 μg/ml pyruvic acid, 1 μl/ml DL-lactic acid (Sigma), 5 mg/ml bovine albumin (ICN Biomedicals), 2 mM L-glutamine, $5 \times 10^{-5}$ M 2-mercaptoethanol, MEM non-essential vitamin solution (Invitrogen), $10^{-4}$M ascorbic acid, 10 μg/ml d-biotin, 30 ng/ml β-estradiol, 60 ng/ml progesterone (Sigma), 20 ng/ml mouse epidermal growth factor (EGF: Becton Dickinson), 10 ng/ml basic fibroblast growth factor (bFGF:Becton Dickinson), $10^3$ units/ml ESGRO (mouse leukemia inhibitory factor: LIF, Invitrogen), 10 ng/ml recombinant rat GDNF (R&D Systems), and 1(v/v)% fetal calf serum (JRH Biosciences). The cells were maintained at 37° C. in an atmosphere of 5% carbon dioxide in air.

(3) Antibody Staining

To confirm the properties of the cells cultured under the culture conditions of (2) above, flow cytometry to examine the expression of conventionally known molecular markers for spermatogenic cells was performed as described below.

Rat anti-EpCAM (G8.8), mouse anti-SSEA-1 (MC-480) (Developmental Studies Hybridoma Bank, University of Iowa), rat antihuman α6-integrin (CD49f) (GoH3), biotinylated antirat β1-integrin (CD29) (Ha2/5), APC-conjugated rat antimouse c-kit (CD117) (2B8) (BD Biosciences), rat anti TDA antibody (EE2) (provided by Dr. Nishimune, Osaka University), or APC-conjugated goat antirat-IgG (Cedarlane Laboratories) was used as primary antibody.

APC-conjugated goat antirat IgG (Cedarlane Laboratories), APC-conjugated streptavidin (BD Biosciences), or Alexa Fluor 633-conjutated goat antimouse IgM (Molecular Probes) was used as secondary antibody. The cell staining technique was performed as previously described (Shinohara T, Avarabock M R, Brinster R L β1-and-α6-integrin are surface markers on mouse spermatogonial stem cells, Proc Natl Acad Sci USA, 1999, vol. 96, pp. 5504-5509). Cells were analyzed with a FACS-Calibur system (BD Biosciences).

(4) Transplantation of Cultured Spermatogonial Stem Cells

Approximately 8 μl of the donor cell suspensions, containing spermatogonial stem cells obtained by the above-described culture method, were injected into the seminiferous tubules of a nude recipient testis. 2 μl of the donor cell suspensions were introduced into the W pup mouse testis through the efferent duct. The injection filled 75-80% of the tubules in each recipient testis. Adult recipient mice were anesthetized by Avertin injection (640 mg/kg).

To count colonies, in recipient mouse tests, recipient mouse testes were recovered 7-8 wk after donor cell transplantation and analyzed by observing fluorescence under UV light. Donor cells were identified clearly because host testis cells had no endogenous fluorescence. A cluster of cells was defined as a colony when it occupied the entire circumference of the seminiferous tubule and had at least 0.1 mm length.

(5) Microinsemination

Sperm derived from cultured cells was collected from inside of the recipient mouse testis, and microinsemination was performed by the method described below.

The seminiferous tubules of transplantation experiment were analyzed in detailed, and the sperm forming cells were collected mechanically. Microinsemination was performed as previously described (Kimura Y, Yanagimachi R, Intracytoplasmic sperm injection in the mouse, Biol Report, 1995, vol. 52, pp. 709-720). Embryos that reached to the four-cell stage after 24 h in culture were transferred to the oviducts of Day 1 pseudopregnant ICR females. Live fetuses retrieved on Day 19.5 were raised by lactating foster ICR mothers.

[2] Results

Hereunder, the results of this experiment performed by the above-described method are shown in (1) to (4) below.

(1) In vitro Culture of Mouse Spermatogonial Stem Cells

Neonatal DBA/2 mouse testis cells were enzymatically dispersed and transferred to gelatin-coated plates in medium containing GDNF, bFGF, EGF, LIF, and FCS. GDNF was known to stimulate spermatogonial stem cell self-renewal in vivo. Other factors are known to affect the proliferation and maintenance of other stem cells, including primordial germ cell (PGC).

Figure 1:
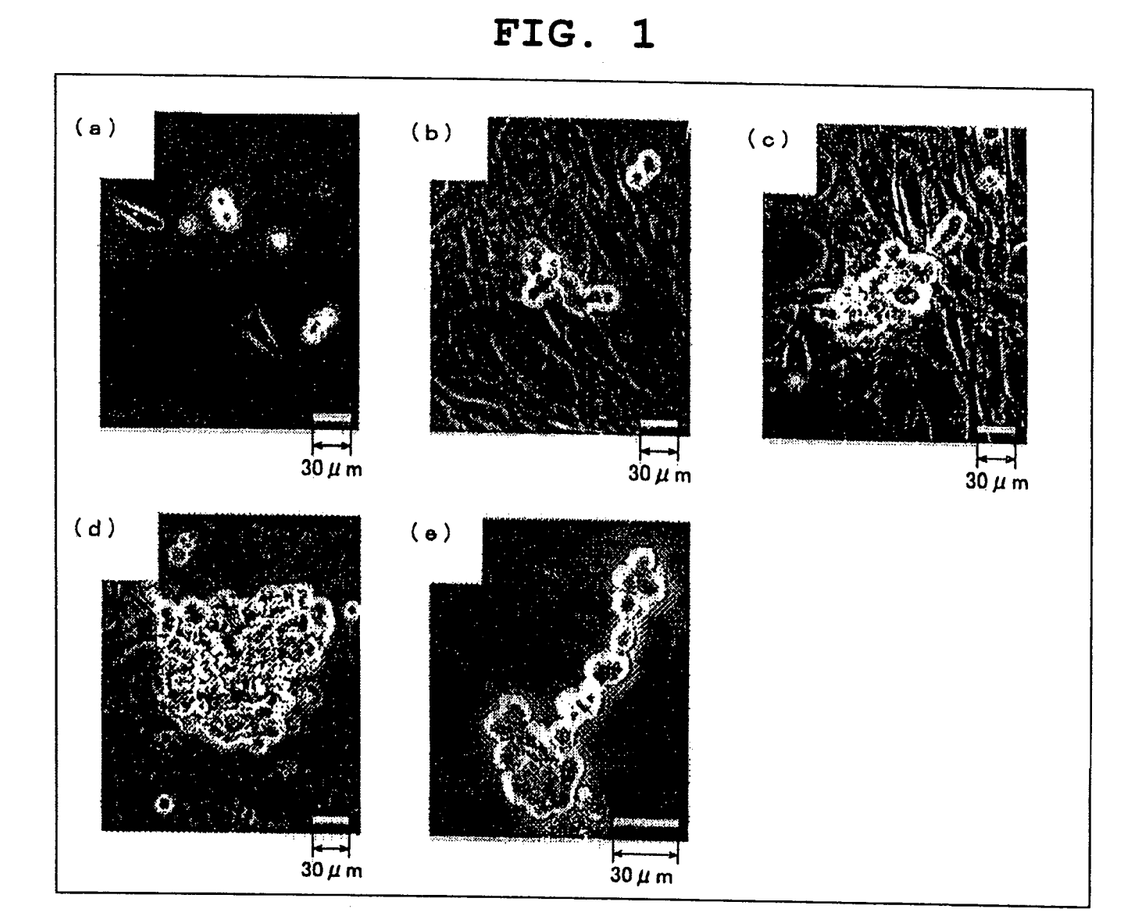

As the results of the cultivation in this experiment, many cells attached to the plate after overnight incubation. But a significant number of germ cells, characterized by their large size and pseudopod, remained floating. The floating cells were passaged to secondary culture plates after vigorous pipetting. Very few germ cells were left on the original gelatin-coated plate, and cells passaged to secondary plates were relatively enriched germ cells (FIG. 1a, arrows). Within 1 wk, the passaged cells proliferated and spread on the bottom of the plate, and round proliferated cells formed colonies on top of the flat cell layer (FIGS. 1b and c). Many of these primary colonies consisted of compact clusters with unclear borders (FIG. 1c). Cell division and colony formation did not occur without above-mentioned growth factors.

Cells were dispersed by trypsin treatment and transferred at intervals of 10-14 days (this interval is called "DIV" for short) to a fresh culture plate (×1 dilution) in vitro. Colonies grew to the original size in about 10 days, and cells were again passaged (×one-half dilution). Although the colonies continued to grow, flat-type somatic cells gradually disappeared after 20 DIV. Therefore, from the second or third passage, the cells were maintained on mitomycin C-inactivated mouse embryonic fibroblasts (MEF) and passaged every 3 to 5 days to fresh MEF at a one-third to one-fourth dilution. By 3 to 4 wk, the cultures remained in a relatively steady state and generated colonies of similar morphology (FIG. 1d). Interestingly, chains of proliferating cells, resembling mitotic spermatogonia in vivo, were occasionally observed after passage (FIG. 1e). Intracellular bridges were observed as shown in FIG. 1e (arrow).

These results were reproducible, and similar cultures were established from 20 or more different experiments. However, colony derivation was influenced by the genetic background of the mouse. Specifically, by starting cultivation from ICR or C57BL/6×DBA/2F1 (BDF1), colonies could be efficiently derived, but the colony derivation from the C57BL/6 or 129/Sv strain was of low efficiency.

Figure 2:
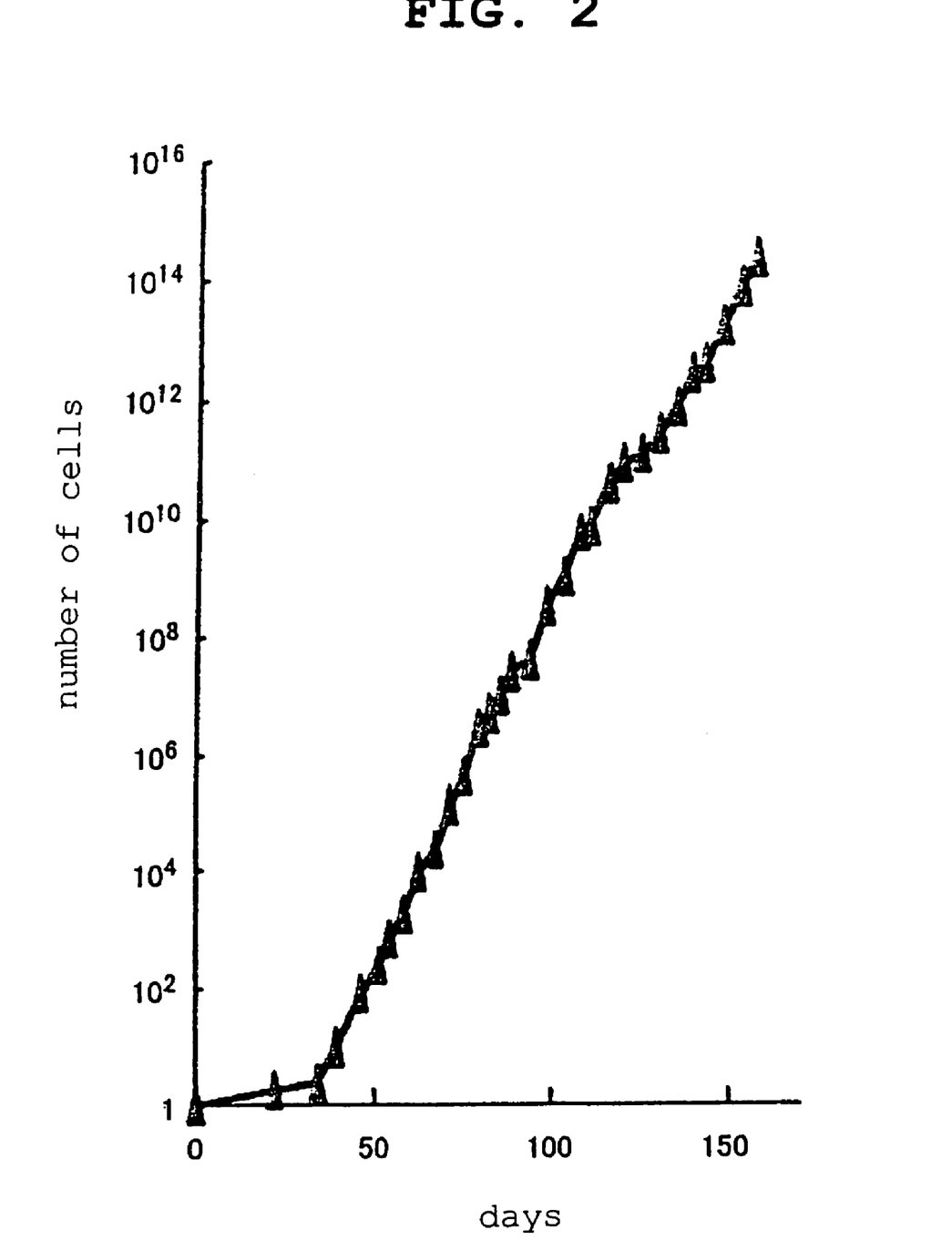
FIG. 2 is a graph showing the proliferation of GS cells cultured in Example 1; specifically, measurements of the number of GS cells that are distinguishable from feeder cells by GFP labeling are shown.
Figure 3:
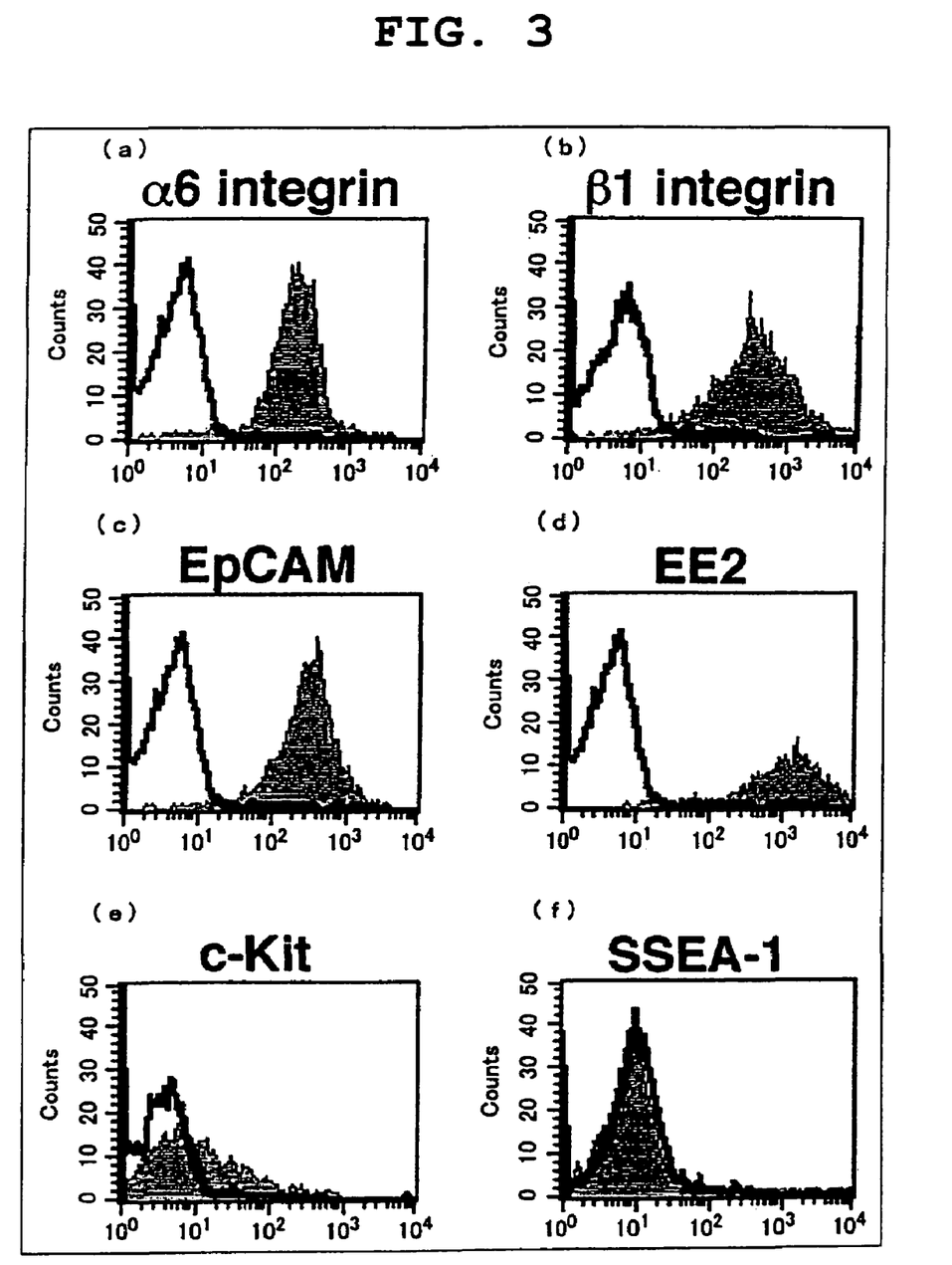

The appearance of growth of cultured cells (i.e., spermatogonial stem cells) in this experiment is shown in the graph of FIG. 2. In this graph, the abscissa indicates the number of days that elapsed after the start of cultivation, and the ordinate indicates the number of cells. As shown in FIG. 2, cell culture was continued for about 5 months, and it was confirmed that cell growth was sustained on a logarithmic scale. Additionally, the number of cells increased about $10^{14}$ folds in 5 months after the start of cultivation.

From the results above, a combination of the growth factors GDNF, bFGF, EGF, and LIF, and leukemia inhibitory factor, was shown to induce an increase in spermatogonia having the potential for stem cells in vitro. Based on this result, the proliferated cells were designated as germ line stem cells (GS cells).

(2) Characteristics of the Cultured Cells

To evaluate the cultured cell characters, testis cells from neonatal Green mouse were used (reference 1). GFP gene was expressed ubiquitously in these mice, including in spermatogonia; therefore, cultured cells including GFP can be distinguished from feeder cells by observation under a UV irradiation. Cell culture was established from the Green mouse, and the surface phenotype of cells including GFP was analyzed by flow cytometry.

The results are shown in FIG. 3(a) to (f). The panels shown in FIG. 3 are the results of analyses performed using molecular markers called α6-integrin, β1-integrin, EpCAM, EE2, c-kit, and SSEA-1 in the order from (a). Note that the white object encircled by the black solid line is the results for the control immunoglobulin, and the gray object is the results for each molecular marker (antibody).

The cultured cells were positive for α6-integrin and β1-integrin (spermatogonial stem cell markers), EpCAM (spermatogonia marker), and EE2 (spermatogonia marker).

Although many cells were negative for c-kit (differentiated spermatogonia marker), weak expression was noted, suggesting that some colonies were differentiating. Nevertheless, adding the c-kit ligand SCF to the culture did not change the phenotype or growth characteristics of the colonies. The cultured cells were completely negative for SSEA-1 (PGC marker). These results indicated that the majority of these cells had an undifferentiated spermatogonia character.

(3) Determination of Stem Cell Activity by Spermatogonial Transplantation

Based on the results of above-described (2), to confirm that the cultured cells are actually spermatogonial stem cells, spermatogonial transplantation was performed, subsequently.

Because there are no clear morphological criteria or specific markers for spermatogonial stem cells, the only reliable assay is confirming restoration of spermatogenesis in infertile animals. For these experiments, three separate cultures (experiments 1, 2, and 3) from Green mice were established. Furthermore, to confirm the growth of stem cells in vitro, the cells were transplanted into seminiferous tubule of an infertile mouse at two different time points, and the number of colonies formed was counted.

Concretely, following culture periods of 29 to 58 days, cells were harvested and transplanted into the seminiferous tubules of busulfan-treated nude mice. After 4 to 21 passages, cells were collected again at 45 to 134 DIV for transplantation to measure the increase in stem cell numbers during this period. Colonies in the transplantation experiments were counted under UV irradiation at 7 to 8 wk after transplantation.

The results were shown in Table 1. Stem cell numbers increased in all three experiments.

TABLE 1

| Experiment | Days after transplantation (number of passages) | Number of cells injected to testis ($\times 10^5$) | Number of colonies in testis (mean ± standard error) | Number of colonies/$10^5$ cells (mean ± standard error) | Increase in number of cells between transplantations (fold increase) | Increase in number of stem cells (fold increase) |
|---|---|---|---|---|---|---|
| 1 | 46 (6) | 2.0 | 33.6 ± 2.0 | 16.8 ± 1.0 | $6.9 \times 10^7$ | $1.9 \times 10^7$ |
|  | 107 (21) | 1.6 | 7.4 ± 2.9 | 4.6 ± 1.8 | 127 | 692 |
|  | 134 (27) | 0.3 | 7.6 ± 4.1 | 25.2 ± 13.8 |  |  |
| 2 | 29 (3) | 3.4 | 67.4 ± 11.1 | 20.1 ± 3.3 | 38.0 | 11.2 |
|  | 45 (7) | 1.6 | 9.5 ± 0.9 | 5.9 ± 0.5 |  |  |
| 3 | 58 (9) | 2.0 | 7.5 ± 3.7 | 3.8 ± 1.9 | $2.0 \times 10^6$ | $4.2 \times 10^6$ |
|  | 113 (22) | 0.4 | 3.2 ± 2.1 | 8.0 ± 5.2 |  |  |

Because the number of stem cells in neonatal testis is 3 or 4 per $10^5$ cells, this result also indicates that stem cells expanded approximately $5 \times 10^{12}$-fold from the initiation of culture to 134 days. In this experiment, the longest culture with stem cell activity, as confirmed by transplantation assay, has been maintained for 134 days with 27 passages ($7 \times 10^{11}$-fold expansion), and the cells kept growing for over ~160 days ($2 \times 10^{14}$-fold expansion in total cell number) (FIG. 2), retaining characteristic morphology. These results show that cells are actively increasing in number.

(4) Restoration of Fertility in Infertile Males Having Cultured Stem Cells Transplanted thereto Finally, to confirm whether the germ cells developed in the transplantation experiments were normal, the inventors attempted to restore fertility to infertile WBB6F1W/Wv (W) by cultured cell transplantation. These mice are congenitally infertile because of a c-kit gene defect.

Two experiments were performed. Testis cells were cultured for 40 days in the first experiment and 91 days in the second experiment, and transplanted into three immune-suppressed allogenic W pup mice (5-10 days old) in both experiments. Forty days after transplantation, one of the recipient W mice in the first experiment was sacrificed and used for histological analysis and in vitro microinsemination. The remaining W recipients were naturally mated with wild-type females to determine whether they restored fertility.

Figure 4:
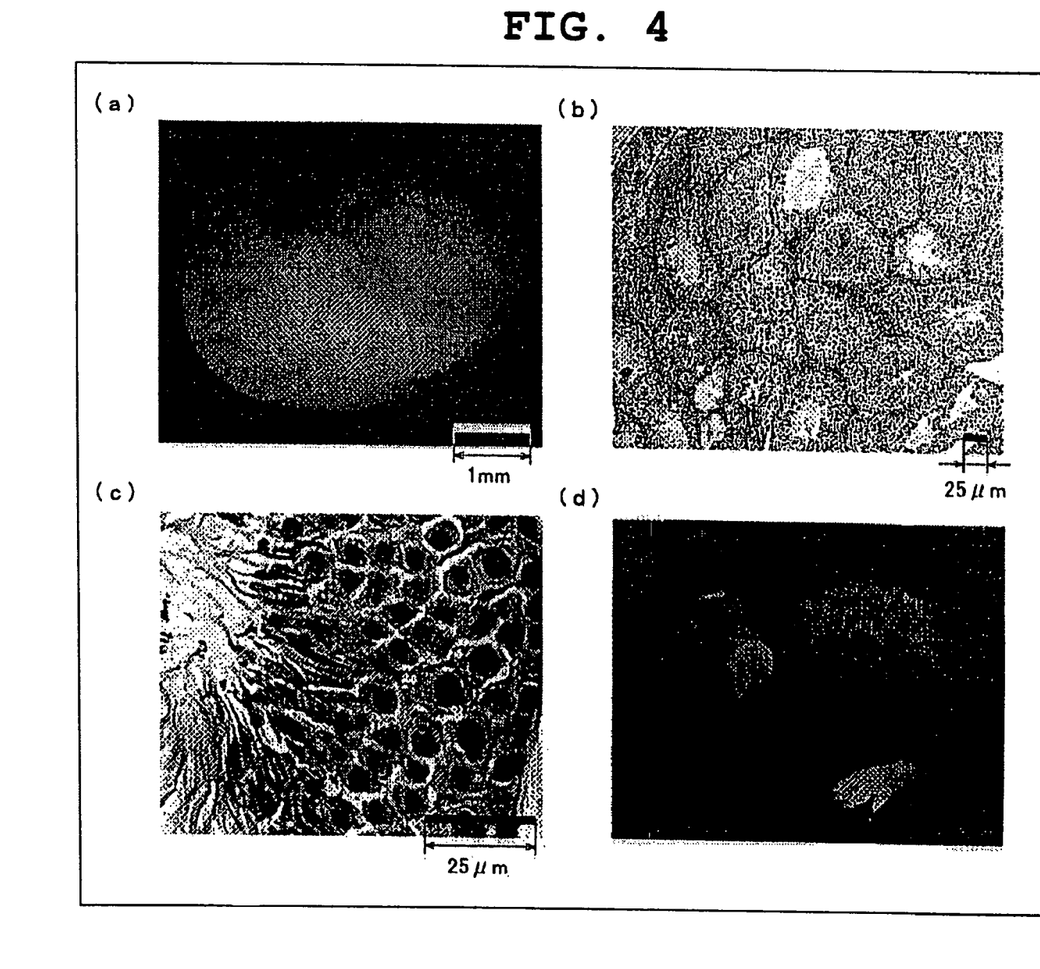
FIG. 4 shows the results of spermatogenesis and offspring preparation from GS cells after spermatogonial transplantation in Example 1. (a) shows the results of an observation of a recipient testis derived from GFP-labeled donor GS cells. (b) and (c) show the results of a histological observation of a W recipient testis; (b) shows the results for normal spermatogenesis, and (c) shows the results for mature sperms, respectively. (d) shows the results for offspring derived from GFP-labeled GS cells, which shows fluorescence under UV irradiation.

Analysis of W recipient testis obtained in this experiment demonstrated extensive colonization by the cultured cells that filled numerous seminiferous tubules with apparently normal spermatogenic cells (FIG. 4a, b). Mature spermatozoa were observed (FIG. 4c). Spermatogenesis in host mice in the transplantation experiment could have come only from cultured donor stem cells because W recipients cannot generate spermatogenesis in their defective stem cells. To generate offspring, 68 live spermatozoa or 139 elongated spermatids were collected from the other W testis and injected into BDF1 oocytes. Of the 207 embryos constructed, 172 (83%) developed to two cells within 24 h in culture. After transfer into the oviducts of 11 pseudopregnant females, a total of 59 pups were born (17 males and 29 females; not including those that were cannibalized by mother mouse after birth). Offspring were also obtained by natural mating. One of the remaining two recipients in the first experiment sired seven offspring (three males and four females) at 74 days after transplantation, and one of the three recipients in the second experiment sired nine offspring (five males and four females) at 91 days after transplantation. The donor origin of the pups in both experiments was confirmed by fluorescence under UV irradiation (FIG. 4d). The offspring were proved to be fertile. Taken together, these results indicate that germ lines differentiated from cultured cells are capable of producing spermatogenesis and normal offspring.

EXAMPLE 2

[1] Experimental Methods and Materials (1) Animals Used in the Experiment

First, the animals used in this experiment are described.

Testis cells were collected from a neonatal pup of DBA/2 mouse by two-step enzymatic digestion in the same manner as Example 1, and were used for cultivation.

W mice (5 to 10 days old) were used as recipients. Female wild C57BL/6 mice were used for mating with the recipients.

The DBA/2, W mice, and C57BL/6 mice were purchased from Japan SLC (Hamamatsu, Japan).

(2) Culture Conditions

Cultured cells (spermatogonial stem cells) were established under the same conditions as Example 1 using isolated testis cells.

The plasmid vector based on the pCXN harboring the neomycin resistance gene and the EGFP structural gene functionally linked to CAG promoter (pCAG-EGFP) was used for gene introduction. For lipofection, spermatogonial stem cells were transfected with Fugene6 transfection reagent (Roche) according to the manufacturer's instruction. Dissociated spermatogonial stem cells were plated at a density of $2\times10^6$ cells/55 cm$^2$ in 7 ml medium and cultured with 9 μg plasmid DNA and 27 μl Fugene6. G418 selection (20-40 μg/ml Geneticin; Invitrogen) was started at 2 days after the transfection. The culture conditions for spermatogonial stem cells in G418 selection were the same as the culture conditions of Example 1, except that G418 was added to the medium. After 10 days selection with G418, culture was passaged. Alternatively, colonies were picked up and expanded clonally. Since the growth of spermatogonial stem cells is affected by the density, individual colonies were mixed with 1,000 untransfected spermatogonial stem cells and transferred to 96 well MEF culture plate. Transduced cells were expanded with repeating G418 selection and mixing procedures. After 2-3 months, surviving colonies were expanded to obtain enough cells numbers for transplantation.

(3) Transplantation of the Cultured Spermatogonial Stem Cells

The spermatogonial stem cells transgened by the above-described method were transplanted to W mouse pups. Approximately 2 μl of the donor cell suspensions ($3-5\times10^7$/ml) was injected into the seminiferous tubules of a W pup recipient mouse through the efferent duct. The injection filled 75 to 80% of the tubules in each recipient testis. Recipients were placed on ice to cause hypothermia-induced anesthesia. 50 μg anti-CD4 antibody (GK1.5) was administrated intraperitoneally on days 0, 2, and 4 after transplantation to induce tolerance to the allogenic donor cells. All animal experimentation protocols were approved by the Institutional Animal Care and Use committee of Kyoto University.

(4) DNA Analysis

As a result of G418 selection, the chromosome DNA of a G418-resistant spermatogonial stem cell colony was analyzed by Southern blotting. Additionally, the recipient male mice were mated with the female wild C57BL/6 mice, and the chromosome DNAs of the offspring thereof were analyzed in the same manner.

Chromosome DNA (8 μg) isolated from G418-resistant spermatogonial stem cells or mouse tail tissue was digested for overnight with SphI, separated by electrophoresis, and blotted onto a nylon membrane (Hybond-N$^+$; Amersham Pharmacia). EGFP probe comprising full-length EGFP cDNA was used for hybridization. Hybridization was performed under common condition as described in Molecular Cloning: A laboratory manual (1989), Cold Spring harbor Laboratory Press, New York, USA, 9.31-9.62 and the like.

[2] Results

Hereunder, the results of this experiment performed by the above-described method are shown below.

(1) Establishment of Transgenic Spermatogonial Stem Cells

Figure 5:
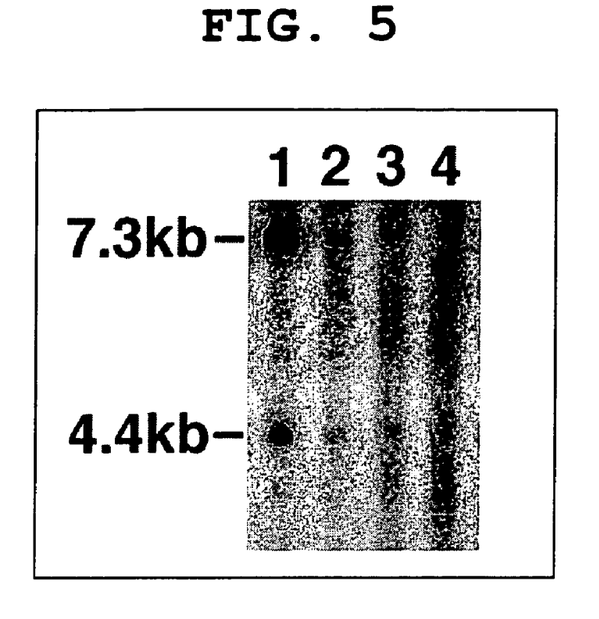
FIG. 5 shows the results of a Southern blotting analysis of chromosome DNAs derived from spermatogonial stem cells incorporating the EGFP gene and from a transgenic animal produced using the spermatogonial stem cells, in Example 2. Lane 1 shows the results for a chromosome DNA derived from spermatogonial stem cells incorporating the EGFP gene, and lanes 2 to 4 show the results for a chromosome DNA derived from the transgenic animal. In all lanes, a 7.3-kb band and a 4.4-kb band were observed as a result of specific hybridization of the EGFP probe.

A plasmid vector based on pCXN harboring the neomycin resistance gene and the EGFP structural gene functionally linked to the CAG promoter (pCAG-EGFP) was introduced to spermatogonial stem cells, and G418 selection was performed, to thereby establish stable clonal transgenic spermatogonial stem cells incorporating the EGFP gene. It was verified by Southern blotting analysis that the EGFP gene was introduced into the genomic DNA of the spermatogonial stem cells (FIG. 5, lane 1).

(2) Preparation of Transgenic Mice

Figure 6:
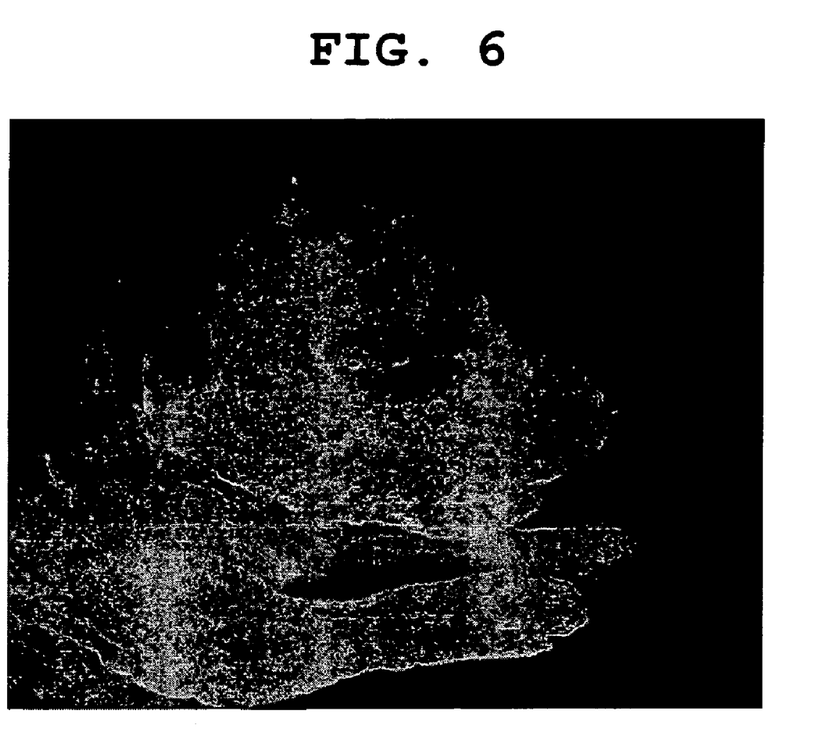
FIG. 6 shows the results of an observation under UV irradiation of a transgenic animal produced according to Example 2. Fluorescence of EGFP derived from the transgene introduced to cultured cells was observed.

Spermatogonial stem cells incorporating the EGFP gene were transplanted to W mice, and the W mice were allowed to spontaneously mate with female wild C57BL/6 mice to obtain offspring thereof. It was verified by Southern blotting analysis that the EGFP gene derived from spermatogonial stem cells was introduced into the genomic DNA of the offsprings (FIG. 5, lanes 2 to 4). Additionally, it was also confirmed by fluorescence under UV irradiation that the offspring is derived from the spermatogonial stem cells incorporating the EGFP gene (FIG. 6).

From these results, it was confirmed that by using the method of the present invention of growing spermatogonial stem cells, an exogenous gene can be introduced to spermatogonial stem cells, and that spermatogonial stem cells stably incorporating the exogenous gene can be selected. Additionally, it was confirmed that an animal incorporating an exogenous gene (transgenic animal) could be produced using the spermatogonial stem cells.

EXAMPLE 3

[1] Experimental Methods and Materials

GS cells (cultured cells) established in the same manner as Example 1 were further cultured using a culture medium containing recombinant human neurturin (manufactured by Wako Pure Chemical Industries), in place of recombinant rat GDNF, at a concentration of 30 ng/mL, to examine whether the growth and colonization of the GS cells would be maintained. Four days after the medium was exchanged with the neurturin-containing medium, the formed colonies were morphologically observed using a phase contrast microscope, and the number of cultured cells was counted.

[2] Results

Figure 7:
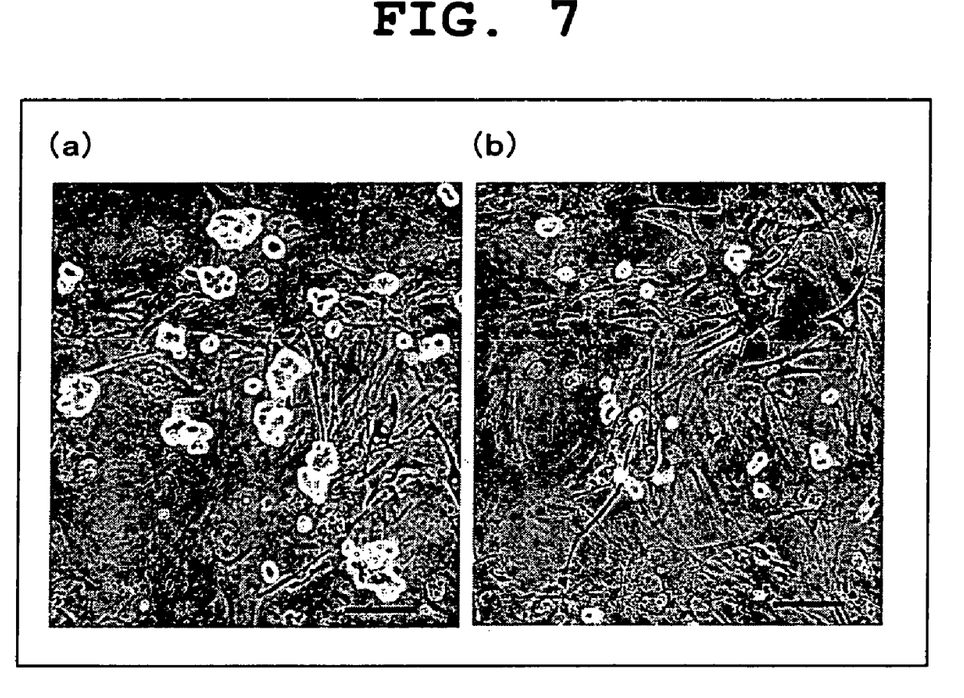
FIG. 7 shows the results of an examination of colonies of spermatogonial stem cell grown using a GDNF-free neurturin-containing medium (a) or a GDNF-free neurturin-free medium (b) in Example 3. In the figure, the lower right bar corresponds to 100 μm.

Even when the established GS cells were cultured using the medium containing neurturin, in place of GDNF, growth of GS cells was confirmed and colonization was observed as with the use of the GDNF-containing medium (FIG. 7a). On the other hand, even when GS cells were cultured in a GDNF-free neurturin-free medium for control, almost no colonization was observed (FIG. 7b).

Additionally, when the established GS cells were cultured in a GDNF-free neurturin-containing medium, the cells showed a 1.3 fold proliferation, from $2.8 \times 10^5$ cells to $3.7 \times 10^5$ cells, based on cell count, in 4 days. In contrast, when the GS cells were cultured in a GDNF-free neurturin-free medium for control, the number of cells decreased to a 0.2 fold level, from $2.8 \times 10^5$ cells to $5.7 \times 10^4$ cells, in 4 days.

INDUSTRIAL APPLICABILITY

According to the method of the present invention, it is possible to grow spermatogonial stem cells, which have not permitted long-term growth in vitro. Thereby, it is possible to effectively utilize spermatogonial stem cells, which have been subject to limitation as to applicability due to the lack of an efficient growing method despite the expectation for application to various fields.

Also, because the spermatogonial stem cells of the present invention obtained by the above-described method have been proliferated to the extent that permits practical application thereof, they can be utilized for developmental engineering in various fields, including in vivo experiments, medical research, biotechnology and the like.

This application is based on a patent application No. 2003-110821 filed in Japan, the contents of which are hereby incorporated by reference.

The invention claimed is:

1. A method of growing mammalian spermatogonial stem cells, which comprises growing mammalian spermatogonial stem cells by culturing the spermatogonial stem cells for at least 3 to 4 weeks on a layer of feeder cells and a medium containing (a) glial cell-derived neurotrophic factor, (GDNF) or neurturin, (b) leukemia inhibitory factor (LIF), and c serum.

2. The method of growing spermatogonial stem cells of claim 1, wherein the medium further contains at least one of epidermal growth factor (EGF) and basic fibroblast growth factor (bFGF).

3. The method of growing spermatogonial stem cells of claim 1, wherein the GDNF or neurturin has a concentration of 0.5 to 50 ng/ml in the medium.

4. The method of growing spermatogonial stem cells of claim 1, wherein the LIF has a concentration of $10^2$ to $10^4$ units/ml in the medium.

5. The method of growing spermatogonial stem cells of claim 2, wherein the EGF has a concentration of 0.5 to 50 ng/ml in the medium.

6. The method of growing spermatogonial stem cells of claim 2, wherein the bFGF has a concentration of 0.5 to 50 ng/ml in the medium.

7. The method of growing spermatogonial stem cells of claim 1, wherein the serum has a concentration of 0.1 to 5(v/v) % in the medium at the start of cultivation of the spermatogonial stem cells, and at a concentration of 0.1 to 20(v/v) % in the medium after passage of the spermatogonial stem cells.

\* \* \* \* \*

UNITED STATES PATENT AND TRADEMARK OFFICE
CERTIFICATE OF CORRECTION

PATENT NO.        : 7,666,673 B2                                            Page 1 of 1
APPLICATION NO.   : 10/553118
DATED             : February 23, 2010
INVENTOR(S)       : Shinohara et al.

It is certified that error appears in the above-identified patent and that said Letters Patent is hereby corrected as shown below:

IN THE CLAIMS

Claim 1, column 22, lines 16-17, "and c serum." should read "and (c) serum."

Signed and Sealed this

Seventeenth Day of August, 2010

David J. Kappos
*Director of the United States Patent and Trademark Office*